(12) United States Patent  
Funabashi

(10) Patent No.: US 7,905,899 B2
(45) Date of Patent: Mar. 15, 2011

(54) NOSE PROTECT

(75) Inventor: Masahiro Funabashi, Koganei (JP)

(73) Assignee: Eight Six Japan Limited Company, Tokyo (JP)

( * ) Notice: Subject to any disclaimer, the term of this patent is extended or adjusted under 35 U.S.C. 154(b) by 702 days.

(21) Appl. No.: 11/589,873

(22) Filed: Oct. 31, 2006

(65) Prior Publication Data

US 2007/0106321 A1    May 10, 2007

(51) Int. Cl.
*A61M 29/00* (2006.01)
*A61F 5/08* (2006.01)
(52) U.S. Cl. ......................... 606/199; 606/196
(58) Field of Classification Search ........... 128/858, 128/857; 606/196, 199, 204.45; 623/10; 602/902
See application file for complete search history.

(56) References Cited

U.S. PATENT DOCUMENTS 4,105,035 A * 8/1978 Rella .................. 606/199
2004/0018792 A1 * 1/2004 Kaizuka .................. 442/327

FOREIGN PATENT DOCUMENTS

| JP | 3-19856 | 4/1991 |
| JP | 7-33775 | 8/1995 |
| JP | 10-127776 | 5/1998 |
| JP | 2000-135234 | 5/2000 |
| JP | 2001-037796 | 2/2001 |
| JP | 2002-519140 | 7/2002 |

* cited by examiner

*Primary Examiner* — Todd E Manahan
*Assistant Examiner* — Ashley Cronin
(74) *Attorney, Agent, or Firm* — Pillsbury Winthrop Shaw Pittman, LLP

(57) ABSTRACT

A nose protect, which is mounted in each of nostrils to thereby reshape the nose, includes a first nostril abutting portion having a first curved surface, coming in surface contact with the inside region of a nasal tip in a preset range; a second nostril abutting portion having a second curved surface, coming in surface contact with the inside region of an ala nasi opposite to the inside region of the nasal tip in a preset range; and a pair of nostril abutting portion connections configured into a thin plate shape that facilitates elastic deformation, coupling the first nostril abutting portion to the second nostril abutting portion, integrally molded out of synthetic resin in which tourmaline powder is mixed with silicon resin.

5 Claims, 3 Drawing Sheets middle portion between the inside region of the nasal tip and the inside region of the ala nasi

NOSE PROTECT

This application is based on Japanese Application No. 2005-130023 filed in Japan on Apr. 27, 2005, the contents of which are hereby incorporated by reference.

BACKGROUND OF THE INVENTION

1. Field of the Invention

This invention relates to a nose protect for reshaping the nose and preventing diseases in the nose.

2. Description of Related Art

In general, an interest in cosmetology increases and a person whose nose is small and low for the size of his face has a considerable interest in rhinoplasty. A person whose nostrils are small has the problem that he breathes with difficulty, in addition to cosmetology. As a conventional technique for making the shape of the nose look attractive, a surgical rhinoplastic operation that plastic is embedded in the nose or silicon is injected into the nose is known. In such a surgical operation, however, the human body is directly damaged and foreign matter is injected to increase a mental burden of a feeling of uneasiness in the operation, such as a failure or a secondary effect. Furthermore, the surgical operation is costly, many days are required for postoperative care, and the possibility of postoperative carcinogenesis cannot be excluded. Thus, the surgical operation fails to provide the technique that is easily applicable to anyone who desires rhinoplasty (nose reshaping).

Consequently, to perform rhinoplasty (nose reshaping), techniques of removably mounting nose-reshaping devices in nostrils without performing the surgical operation have recently been proposed as the ones that lessen mental, economical, and physical burdens and can be used readily and rapidly. Conventional nose-reshaping devices removably mounted in nostrils so that the nose can be reshaped without performing the surgical operation are disclosed, for example, in Japanese Patent Kohyo No. 2002-519140, Japanese Patent Kokai Nos. 2001-37796 and 2000-135234, Japanese Utility Model Publication Nos. Hei 07-33775 and Hei 03-19856, and Japanese Patent Kokai No. Hei 10-127776.

The nose-reshaping device set forth in Kohyo No. 2002-519140 is designed to have one end portion coming in contact with the inside of a nasal tip in the vestibule of the nose and the other end portion coming in contact with the inside of an ala nasi in the vestibule of the nose, provided to an elastic-deformable, slender arcuate body, and a top portion coming in contact with a part different from the other end portion coming in contact with the inside of the ala nasi in the vestibule of the nose. The nose-reshaping device set forth in Kokai No. 2001-37796 is designed to have a circular external end portion coming in contact with the inside of the nasal tip in the vestibule of the nose and an internal end portion supporting the inside of the ala nasi in the vestibule of the nose, provided to an elastic-deformable, slender rod-shaped body. The nose-reshaping device described in Kokai No. 2000-135234 is designed to have a reshaping cap inserted in the nostril and abutting on the bridge of the nose, a supporting cap abutting on the rear wall of the nostril, and a connecting rod that interconnects the reshaping cap and the supporting cap and that is capable of expansion and contraction. The nose-reshaping device described in Publication No. Hei 07-33775 is made with a flexible material and is constructed so that the entire body is shaped like a slender strip, both end portions are rounded, and the section has a flat or wedge shape in which one side is smaller in thickness than the other. The nose-reshaping device set forth in Publication No. Hei 03-19856 is constructed with a combination of a U-shaped base plate having rack-like teeth on the inside surface and a plate-spring inverted-V-shaped upper plate whose top is round, having the rack-like teeth on the outside surface so that the meshing position of the rack-like teeth is adjusted and thereby the entire height can be controlled. The nose-reshaping device set forth in Kokai No. Hei 10-127776 is configured like a circular, elliptical, or polygonal cylinder and is inserted into the nostril so that the nostril can be enlarged.

However, the nose-reshaping device set forth in each of Kohyo No. 2002-519140, Kokai Nos. 2001-37796 and 2000-135234, and Publication No. Hei 07-33775 is configured like a nearly slender rod, ranging from the end portion coming in contact with the inside of the nasal tip in the vestibule of the nose to the end portion coming in contact with the inside of the ala nasi, so that the contact area of the end portion coming in contact with the inside of the nose is reduced. Consequently, in the case where the nose-reshaping device is configured using a material that facilitates elastic deformation, the nose-reshaping device, after being mounted in the nostril, becomes liable to come off because of a shock from the exterior or internal moisture. When a material in which elastic deformation is difficult is used, there is the fear that the inside part of the nose coming in contact with each end portion is damaged by the shock from the exterior. In the nose-reshaping device described in Publication No. Hei 07-33775, it is also proposed that an elastic protector, such as a sponge, is attached to the end portion coming in contact with the inside part of the nose to thereby prevent the damage of the nose. However, the elastic protector must be provided as an independent member, and thus the number of parts is increased and the cost is raised accordingly, with the result that mounting is complicated. The sponge used in the elastic protector cannot be used over and over again from the viewpoint of its strength and as a result, the cost is further raised.

According to the nose-reshaping device described in each of Publication No. Hei 03-19856 and Kokai No. Hei 10-127776, by contrast, the entire device is configured into an annular shape with a preset width, and hence the areas of the end portions coming in contact with the insides of the nasal tip in the vestibule of the nose and of the ala nasi can be relatively enlarged. However, since this nose-reshaping device is configured into the annular shape with uniform width and thickness as a whole, it is difficult to mount the device in the nostril by elastic deformation. Moreover, when the contact area in the nose is enlarged, cutaneous respiration becomes impossible and comfortableness is impaired. The device is susceptible to contamination to propagate various germs, and this tends to breed rhinitis.

Furthermore, any of the conventional nose-reshaping devices set forth in the above prior art references is configured so that it is difficult to be removed and instruments, such as tweezers, must be used in the nostril. This is inconvenient for dismounting the device. In recent years, persons contracting nasal diseases, such as rhinitis, nasal allergy, and hay fever, have increased. Such nasal diseases are liable to be contracted when eyes and a mucosa in the nasal cavity react oversensitively to pollen, house dust, and exhaust gases. When the blood flow of the mucosa in the nasal cavity is insufficient, fine dust and germs that are not completely removed by vibrissae, in drawn air, cannot be eliminated and clarified by the mucosa, are carried to the choanae by the transportation of mucosal glandular hair, and are sent to the throat and respiratory organs such as the bronchi and lungs. As a result, there is the fear that respiratory diseases become liable to be produced. In order to obviate such nasal diseases, mask-wearing persons have recently been increasing. However, everyday wear of the mask impairs shapeliness of a personal figure and is liable to constitute an obstacle to living. In addition, the conventional nose-reshaping devices set forth in the above references fail to have functions of warding off nasal diseases.

SUMMARY OF THE INVENTION

An object of the present invention is to provide a nose protect which can be mounted in a state where it is hard to come off, without damaging the inner wall of the nose, is mounted so that a mounted state is not noticed from outward appearance, can be easily mounted and dismounted without using instruments, can be used over and over again, is capable of reshaping the nose without performing the surgical operation, and is capable of preventing nasal diseases.

In order to achieve the above object, the nose protect according to the present invention, which is mounted in each of the nostrils to thereby reshape the nose, comprises a first nostril abutting portion having a first curved surface, coming in surface contact with the inside region of a nasal tip in a preset range; a second nostril abutting portion having a second curved surface, coming in surface contact with the inside region of an ala nasi opposite to the inside region of the nasal tip in a preset range; and a pair of nostril abutting portion connections configured into a thin plate shape that facilitates elastic deformation, coupling the first nostril abutting portion to the second nostril abutting portion, integrally molded out of synthetic resin.

In the nose protect according to the present invention, it is desirable that the synthetic resin includes tourmaline or germanium powder mixed with silicon resin.

In the nose protect according to the present invention, it is desirable that at least one of the first curved surface in the first nostril abutting portion, the second curved surface in the second nostril abutting portion, and the pair of nostril abutting portion connections is provided with a group of fine air holes.

In the nose protect according to the present invention, it is desirable that the pair of nostril abutting portion connections is curved in a convex shape so as to be farthest away from each other at the middle part.

In the nose protect according to the present invention, it is desirable that one end of the first curved surface in the first nostril abutting portion is provided with a plate-shaped knob portion.

According to the present invention, it is possible to provide a nose protect which can be mounted in a state where it is hard to come off, without damaging the inner wall of the nose, is mounted so that a mounted state is not noticed from outward appearance, can be easily mounted and dismounted without using instruments, can be used over and over again, is capable of reshaping the nose without performing the surgical operation, and is capable of preventing nasal diseases.

These and other features and advantages of the present invention will become apparent from the following detailed description of the preferred embodiment when taken in conjunction with the accompanying drawings.

DETAILED DESCRIPTION OF THE PREFERRED EMBODIMENT

Figure 1A:
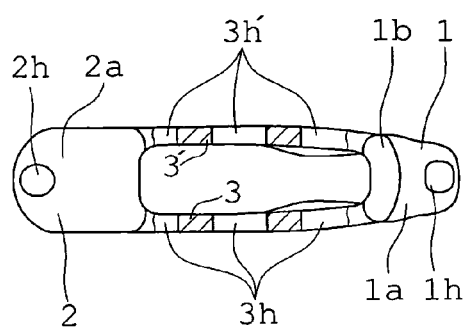
FIGS. 1A, 1B, 1C, and 1D are a front view, a plan view, a left side view, and a right side view, respectively, showing the nose protect of one embodiment in the present invention.
Figure 1B:
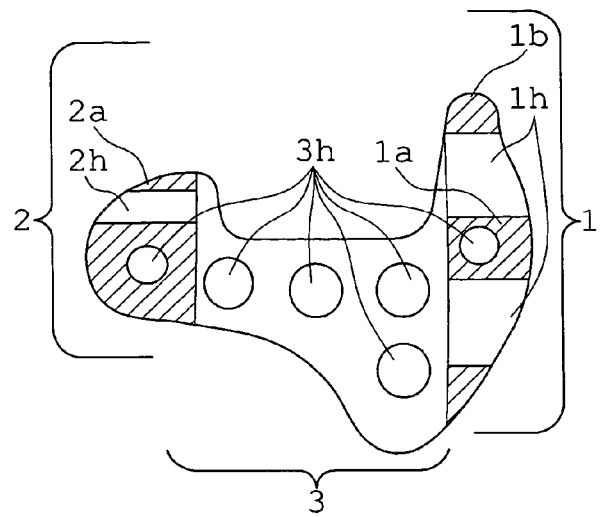
Figure 1C:
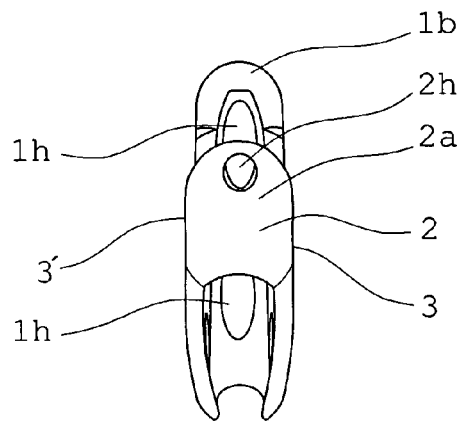
Figure 1D:
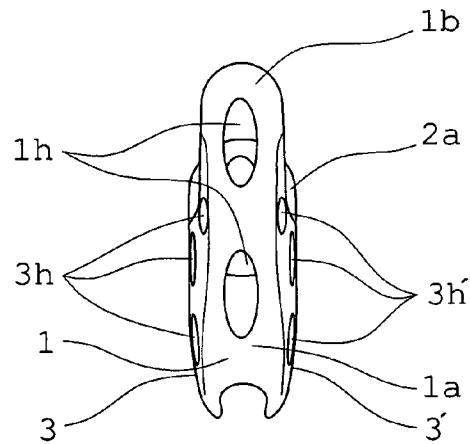
Figure 2A:
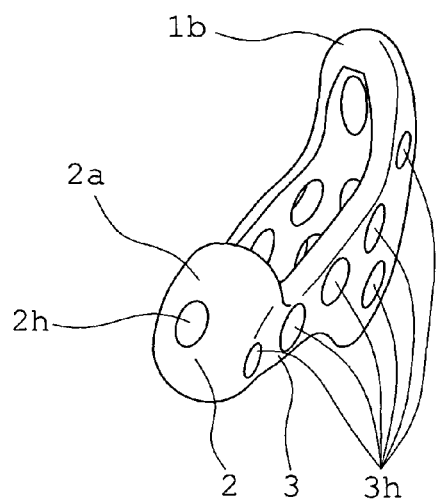
FIG. 2A is a perspective view showing the nose protect viewed diagonally from the upper left side of the nose protect of FIG. 1B.
Figure 2B:
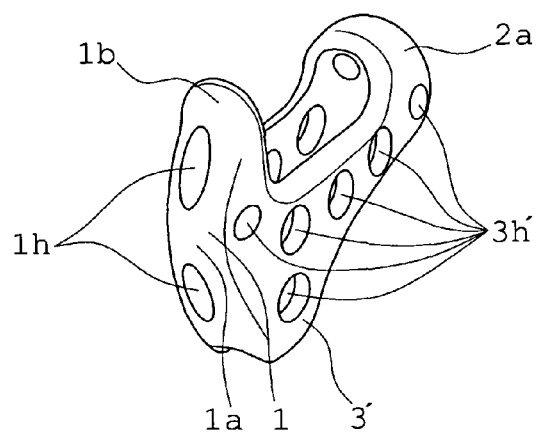
FIG. 2B is a perspective view showing the nose protect in a state where the nose protect of FIG. 2A is rotated by 180°.
Figure 2C:
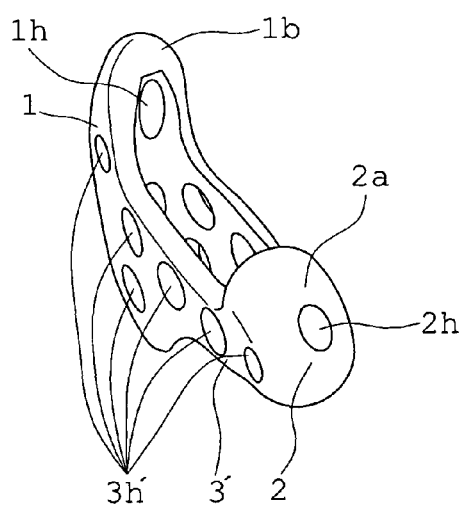
FIG. 2C is a perspective view showing the nose protect viewed diagonally from the front left side of the nose protect of FIG. 1C.
Figure 2D:
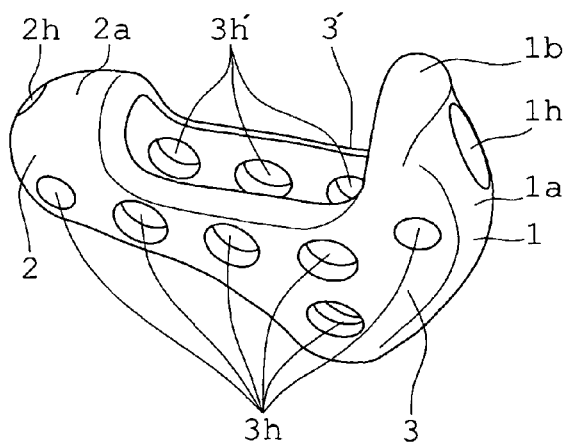
FIG. 2D is a perspective view showing the nose protect viewed diagonally from the upper side of the nose protect of FIG. 2B.
Figure 3A:
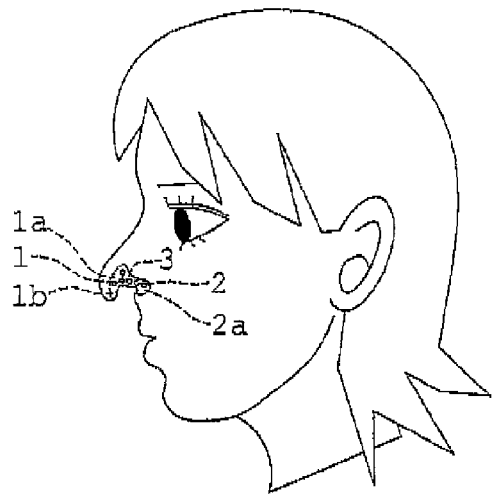
FIGS. 3A, 3B, and 3C are explanatory views in a state where the nose protect of the embodiment is mounted in nostrils, showing a mounted state viewed from the side of the face, a mounted state where the nasal portion is viewed from the upper side, and a mounted state where the nasal portion is viewed from the lower side, respectively.
Figure 3B:
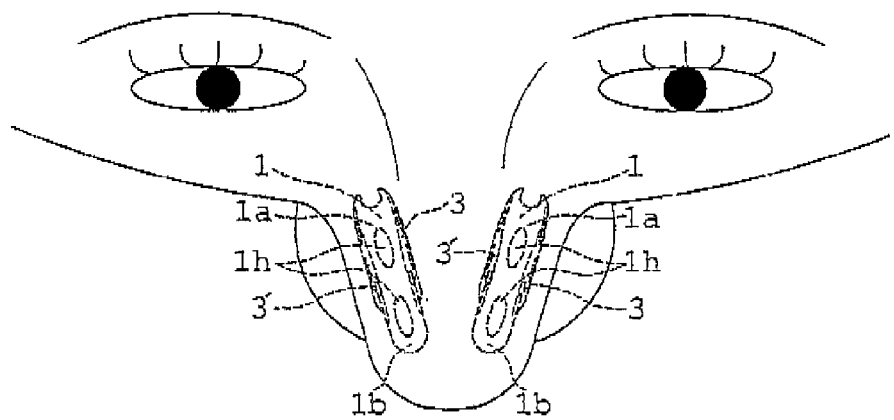
Figure 3C:
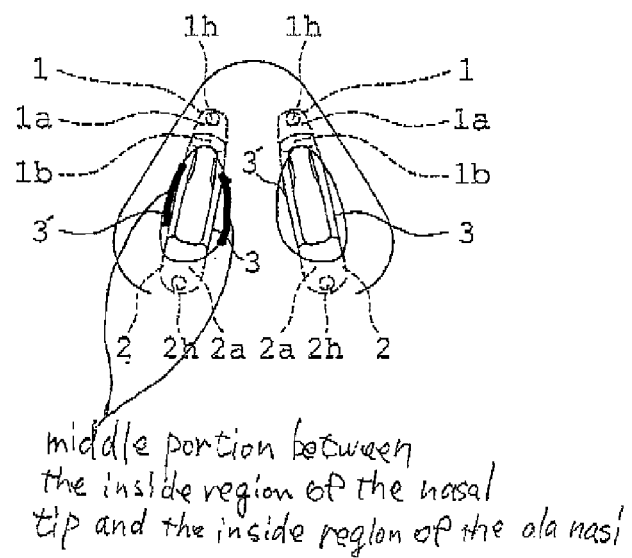

In the following, a description will be given of the nose protect used in one nostril, for convenience of explanation. The nose protect of the embodiment comprises a first nostril abutting portion 1, a second nostril butting portion 2, and a pair of nostril abutting portion connections 3 and 3', integrally molded out of synthetic resin. The first nostril abutting portion 1 has a first curved surface 1a curved and configured so as to come in surface contact with the inside region of the nasal tip in a preset range. The second nostril abutting portion 2 has a second curved surface 2a curved and configured so as to come in surface contact with the inside region of the ala nasi opposite to the inside region of the nasal tip in a preset range. The pair of nostril abutting portion connections 3 and 3' is configured into a thin plate shape that facilitates elastic deformation, coupling the first nostril abutting portion 1 to the second nostril abutting portion 2. The pair of nostril abutting portion connections 3 and 3' is also curved in a convex shape so as to be farthest away from each other at the middle part. The first curved surface 1a, the second curved surface 2a, and the pair of nostril abutting portion connections 3 and 3' are provided with a group of fine air holes 1h, 2h, and 3h and 3h'. One end of the first curved surface 1a is provided with a plate-shaped knob portion 1b.

For the material of the nose protect of the embodiment, styrene-based silicon resin is used which is suited for standards relating to medical sanitation and is harmless and safe for the human body. With this silicon resin, powder particles of tourmaline are mixed in a preset proportion (for example, 15%).

Reference is made to the case where the nose protect of the embodiment constructed as mentioned above is mounted in each nostril. The nose protect of the present invention is mounted in the nostril to thereby reshape a nasal cartilage portion. Therefore, the nose protect is configured so that a distance from the first curved surface 1a to the second curved surface 2a is longer than that from the inside surface of the nasal tip of the nostril, in which the nose protect is mounted, to the inside surface of the vestibule of the nose. The first nostril abutting portion 1, the second nostril abutting portion 2, and the distance from the first curved surface 1a to the second curved surface 2a can be designed according to an individual difference in the shape and size of the nose whose reshaping is desired and the size of each nostril in which the nose protect is inserted, before reshaping. The nose protect of the embodiment is also applicable to a person who does not require the reshaping of the nose and only intends to prevent a nasal disease such as nasal allergy. In this case, it is only necessary to design the strength of the material and the distance from the first curved surface 1a to the second curved surface 2a so that surface contact is made to the extent that the nose is not deformed by the first curved surface 1a of the first nostril abutting portion 1 and the second curved surface 2*a* of the second nostril abutting portion 2.

The nose protect is inserted in the inside of the vestibule of the nose from each anterior naris in such a way that the first curved surface 1*a* faces the nasal tip side and the second curved surface 2*a* faces the ala nasi side while the knob portion 1*b* is held with fingers. In this case, the nostril abutting portion connections 3 and 3' are configured into a thin plate shape that facilitates elastic deformation, and thus the nose protect is such that the nostril abutting portion connections 3 and 3' are elastically deformed with ease. After the nose protect is inserted at a preset position inside the vestibule of the nose from the anterior naris, the knob portion 1*b* is released from finger holding. Whereby, mounting is completed.

In a mounted state, the first curved surface 1*a* brings the inside region of the nasal tip into pressure contact with the surface in a preset range and at the same time, the second curved surface 2*a* brings the inside region of the vestibule of the nose into pressure contact with the surface in a preset range. Whereby, the nasal cartilage portion is reshaped into a desired height, and the balance of the nose against the face is kept fairly aesthetical. The knob portion 1*b* is incorporated in an exit-side region inside the nasal tip. The pair of nostril abutting portion connections 3 and 3' is elastically deformed in a mutually separating direction and thereby is capable of coming in contact with a region in the middle between the inside region of the nasal tip in the nostril and the inside region of the vestibule of the nose.

In the mounted state, as mentioned above, the first curved surface 1*a* brings the inside region of the nasal tip into pressure contact with the surface in a preset range and the second curved surface 2*a* brings the inside region of the vestibule of the nose into pressure contact with the surface in a preset range. Specifically, in the nose protect of the embodiment, the first nostril abutting portion 1 and the second nostril abutting portion 2 are configured so that the nose protect is supported in a wide range by the elasticity of cartilage in each nostril. Consequently, even in the cases where there are vibrations and shocks due to meals and sports, and moisture due to bathing and nasal mucus, the shift of the nose protect at the contact surface is not caused and the mounted state can be maintained without any trouble that the nose protect shifts or deviates from the mounting position. Even though the first curved surface 1*a* or the second curved surface 2*a* is brought into pressure contact with the inside region of the nasal tip or the inside region of the vestibule of the nose by a strong force to some extent, the curved surface comes in contact over the preset range, and the strong force is not exerted at one place. Thus, it is avoidable that the inside of the nose is damaged.

The first curved surface 1*a*, the second curved surface 2*a*, and the pair of nostril abutting portion connections 3 and 3' are provided with the group of air holes 1*h*, 2*h*, and 3*h* and 3*h*', and hence even when the nose protect comes in contact with the inside of each nostril, the contact region of the inside of the nose is not hermetically sealed and cutaneous respiration can be practiced. Consequently, even when the nose protect is mounted for a long time, it is hard to breed rhinitis, and a clean state where various germs are hard to propagate can be maintained.

The nose protect of the embodiment is integrally molded out of resin mixing powder particles of tourmaline in a preset proportion with silicon resin, as the material. The molding of the nose protect from silicon resin facilitates the elastic deformation in mounting and dismounting. Moreover, silicon resin functions as a low-allergy and unstimulating cushion material. Hence, the nose can be further protected from the damage to the inside of the nose and allergy inflammation can be prevented so that the nose protects can be used from infants who have delicate skin to aged persons, irrespective of age. In addition, in the nostrils in which moisture and temperature are properly maintained, tourmaline mixed as powder particles with silicon resin reacts to stimulation to discharge minus ions so that far-infrared radiation thus produced acts on a submucous capillary, the blood flow of the mucosa in the nasal cavity is facilitated, fine dust and germs can be easily eliminated through the mucosa, and the symptom of rhinitis is alleviated. Tourmaline also has an electrical adsorbing function so that, for example, pollen in air is adsorbed to block penetration into the interior of the nostrils. Thus, according to the nose protect of the embodiment, by mounting it, allergic rhinitis, as antigens with pollen, Mycota, ticks, house dust, dirt, and dust, can be restrained in addition to reshaping the nose, and further, by the adsorbing function of tourmaline, the penetration of germs into the throat, bronchi, and lungs can be blocked to prevent respiratory diseases. When the blood flow of the mucosa in the nasal cavity is facilitated by the nose protect of the embodiment, a preset treatment substance can be easily absorbed from the nasal cavity.

Also, for the nose protect of the embodiment, it is possible to apply a material that germanium powder, instead of tourmaline powder, is mixed with silicon resin. Germanium has the function that when the temperature of the contact surface is beyond a preset value, minus ions are discharged and a bioelectric current in the body is normalized to facilitate the flow of the blood. Hence, even when the nose protect is configured by mixing the germanium powder with silicon resin, the flow of the blood of the mucosa in the nasal cavity is facilitated so that the same effect as in tourmaline can be brought about. Consequently, the nose protect of the embodiment can also be applied to disease treatment that it is effective to absorb the a preset treatment substance from the nasal cavity.

When the nose protect of the embodiment is dismounted from each nostril, the knob portion 1*b* is held with fingers and is pulled. Whereupon, while the pair of nostril abutting portion connections 3 and 3' is elastically deformed, the nose protect is easily pulled out from the nostril.

The nose protect of the embodiment, as mentioned above, is integrally molded by using silicon resin. Hence, deposits, such as mucus, adhering to silicon resin can be cleanly removed with a detergent or liquid soap, and the nose protect is dried after cleaning and thereby can be returned to a state before mounting. The nose protect of the embodiment, therefore, can be used over and over again in a sanitary state. In the cleaning of the nose protect of the embodiment, it is good practice that, for example, a detergent for vegetables or tableware is mixed by a proper amount in a 50~150-ml-sized jar or PET bottle, half-filled with water, and then the nose protect is put into the bottle so that after the bottle is shaken several times, the nose protect is finally washed with water. Alternatively, the nose protect is washed with medicated soap by hands, without using the jar or PET bottle, and thereby dirt particles adhering to fine parts like air holes can be easily removed.

According to the nose protect of the embodiment, as described above, the nose protect can be readily mounted in a preset region of each nostril, and is capable of reshaping the nose while keeping a stable mounted state without coming off even when there are vibrations, shocks, and moisture due to meals, bathing, sports, and nasal mucus. Moreover, there is not any fear of damaging the nostril. The mounted nose protect is not noticed from outward appearance. Further, even when the nose protect is mounted for a long time, it assists cutaneous respiration and can be kept in a clean state. By mounting the nose protect, allergic rhinitis due to pollen and respiratory diseases can be restrained and prevented. Further, the nose protect can be applied to disease treatment that it is effective to absorb the a preset treatment substance from the nasal cavity. Still further, the nose protect can be readily removed from the nose with fingers without using instruments. The nose protect can be easily cleaned and thereby can be used over and over again in a sanitary state.

The nose protect of the present invention is useful in a cosmetic field in which it is desired to reshape the nose without performing the surgical operation and a medical field in which it is desired to provide prescriptions for disease treatment which is effective for the restraint of allergic rhinitis, the prevention of respiratory diseases, and the absorption of a preset treatment substance from the nasal cavity.

What is claimed is:

1. A nose protect which is mounted in each of nostrils to thereby reshape a nose, the nose protect comprising:
    a first nostril abutting portion having a first curved surface that is convex outwardly from a near end to a far end thereof, to come in surface contact with an inside region of a nasal tip in a preset range, the near end of the first curved surface being designed to be positioned nearer to an entrance of the nostril and the far end of the first curved surface being designed to be inserted farther from the entrance of the nostril;
    a second nostril abutting portion having a second curved surface that is convex outwardly from a near end to a far end thereof, to come in surface contact with an inside region of an ala nasi opposite to the inside region of the nasal tip in a present range, the near end of the second curved surface being designed to be positioned nearer to an entrance of the nostril and the far end of the second curved surface being designed to be inserted farther from the entrance of the nostril; and
    a pair of nostril abutting portion connections formed as two thin plates, respectively, with a thickness substantially smaller than each thickness of the first nostril abutting portion and the second nostril abutting portion, for facilitating elastic deformation,
    wherein the near end of the first curved surface of the first nostril abutting portion is provided with a knob portion that is convex along its outer surface,
    wherein the pair of abutting portion connections couple the first nostril abutting portion to the second nostril abutting portion such that a plate surface of one of the nostril abutting portion connections continuously extends from one side face of the first nostril abutting portion to one side face of the second nostril abutting portion and a plate surface of another of the nostril abutting portion connections continuously extends from an opposite side face of the first nostril abutting portion to an opposite side face of the second nostril abutting portion,
    wherein a side edge of each of the nostril abutting portion connections between the near end of the first curved surface and the near end of the second curved surface forms a flat-bottomed recess contour so that, in a state where the nose protect is mounted in the nostril with the first curved surface of the first nostril abutting portion being in surface contact with the inside region of the nasal tip and the second curved surface of the second nostril abutting portion being in surface contact with the inside region of the ala nasi, the nostril butting portion connections are elastically deformed with ease in mutually separating directions, to come in contact, in a vestibule of the nose, with a middle portion between the inside region of the nasal tip and the inside region of the ala nasi, and
    wherein the first nostril abutting portion, the second nostril abutting portion, and the pair of nostril abutting portion connections are integrally molded out of synthetic resin.

2. A nose protect according to claim 1, wherein the synthetic resin includes tourmaline powder mixed with silicon resin.

3. A nose protect according to claim 1, wherein at least one of the first curved surface in the first nostril abutting portion, the second curved surface in the second nostril abutting portion, and the pair of nostril abutting portion connections is provided with a group of fine air holes.

4. A nose protect according to claim 3, wherein the pair of nostril abutting portion connections are curved in a convex shape so as to be farthest away from each other at a middle part.

5. A nose protect according to claim 1, wherein the pair of nostril abutting portion connections are curved in a convex shape so as to be farthest away from each other at a middle part.

* * * * *